United States Patent [19]

Boehme et al.

[11] Patent Number: 4,849,532
[45] Date of Patent: Jul. 18, 1989

[54] PROCESS FOR THE PREPARATION OF A CYCLOALIPHATIC DIEPOXIDE

[75] Inventors: Georg Boehme; Willi Hofen, both of Rodenbach; Andreas Grund, Darmstadt; Heinrich Petsch; Guenter Prescher, both of Hanau, all of Fed. Rep. of Germany

[73] Assignee: Degussa Aktiengesellschaft, Frankfurt, Fed. Rep. of Germany

[21] Appl. No.: 166,786

[22] Filed: Mar. 2, 1988

Related U.S. Application Data

[63] Continuation of Ser. No. 890,441, Jul. 30, 1986, abandoned.

[30] Foreign Application Priority Data

Aug. 5, 1985 [DE] Fed. Rep. of Germany ....... 3528002

[51] Int. Cl.⁴ .......................................... C07D 301/14
[52] U.S. Cl. .................................... 549/525; 549/526; 549/541
[58] Field of Search ........................ 549/525, 541, 526

[56] References Cited

U.S. PATENT DOCUMENTS

| | | | |
|---|---|---|---|
| 3,030,336 | 4/1962 | Greenspan et al. | 260/47 |
| 3,351,635 | 11/1967 | Koller | 549/529 |
| 3,458,536 | 7/1969 | Setzler | 549/541 |
| 4,059,619 | 11/1977 | Prescher et al. | 260/502 R |
| 4,101,570 | 7/1978 | Kruger et al. | 260/502 R |
| 4,113,747 | 9/1978 | Prescher et al. | 549/541 |
| 4,137,242 | 1/1979 | Prescher et al. | 549/541 |

FOREIGN PATENT DOCUMENTS

| | | | |
|---|---|---|---|
| 56932 | 8/1982 | European Pat. Off. | 549/525 |
| 061393 | 9/1982 | European Pat. Off. . | |
| 090239 | 3/1983 | European Pat. Off. . | |
| 1203463 | 8/1963 | Fed. Rep. of Germany . | |
| 1173658 | 7/1964 | Fed. Rep. of Germany | 549/525 |
| 2519289 | 11/1976 | Fed. Rep. of Germany . | |
| 2519290 | 11/1976 | Fed. Rep. of Germany . | |
| 2752920 | 5/1979 | Fed. Rep. of Germany | 549/525 |
| 1048318 | 11/1966 | United Kingdom | 549/525 |
| 1518227 | 7/1978 | United Kingdom . | |
| 2008593 | 6/1979 | United Kingdom . | |
| 2019845 | 11/1979 | United Kingdom . | |
| 2109797 | 6/1983 | United Kingdom . | |

OTHER PUBLICATIONS

Hackh's Chemical Dictionary, p. 498, "peracid", 1968.

Primary Examiner—Richard L. Raymond
Attorney, Agent, or Firm—Beveridge, DeGrandi & Weilacher

[57] ABSTRACT

The diepoxide of the formula:

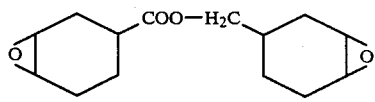

can be prepared from the corresponding diolefin in a technically simple manner by means of perpropionic acid in a benzene solution. The solution can also be employed in unpurified form with certain maximum contents of 1.5 weight percent of hydrogen peroxide, 1.5 weight percent of water, and of about 800 ppm of mineral acid.

6 Claims, 2 Drawing Sheets

PROCESS FOR THE PREPARATION OF A CYCLOALIPHATIC DIEPOXIDE

This application is a continuation of application Ser. No. 890,441 filed Jul. 30, 1986, now abandoned.

The present invention relates to a process for the preparation of a cycloaliphatic diepoxide of the formula:

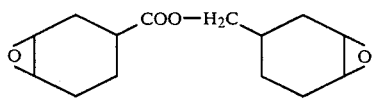 (I)

by epoxidation of a diolefin of the formula:

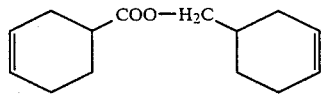 (II)

with a percarboxylic acid in an organic solvent. The invention further relates to the processing of the reaction mixture thus formed to obtain the desired compounds.

The cycloaliphatic diepoxide of the above-mentioned structure has found increasing application as a component of epoxy resins which are particularly suitable as insulation and sealing compositions in the electrical and electronics sector, as well as for radiation curable lacquering and coating systems. Because they do not contain solvents, the latter are of particular interest as they have a very low environmental impact.

The preparation of epoxides by reacting olefins with chlorine in an alkaline medium and subsequent treatment with bases has been known for a long time (Ullmann's Enzklopädie der technischen Chemie, 3rd ed., Vol. 10, page 565). The major disadvantage of this previously described process resides in the substantial amounts of environmentally damaging waste water, which necessarily results from this process. It is further known that ethylene can be epoxidized in high yields in the gas phase with molecular oxygen utilizing silver containing catalysts. This process is unsuitable for other olefins, however, because of its lack of selectivity.

Furthermore, olefins can be converted into corresponding epoxides by reaction with hydroperoxides, which can be obtained from hydrocarbons such as, for example, isobutane or ethylbenzene by oxidation with air in the presence of a catalyst containing vanadium molybdenum, or tungsten compounds (U.S. Pat. No. 3,351,635). This previously known method has the major drawback in addition to the need for separation of the catalyst system; the alcohol that is obtained in an equimolar amount from hydroperoxide as a coupled product, when it is not economically usable, can be recycled into hydroperoxide only with considerable technical expenditure.

The previously mentioned disadvantages can be partially avoided or prevented by means of the "Prileschajew reaction" (N. Prileschajew, Ber. Dtsch. Chem. Ges. 42, 4811 (1909)). This, in essence, is the reaction of an olefin with an organic percarboxylic acid. It is recognized that the use of, e.g. performic acid forms explosive mixtures at relatively high concentrations, and produces considerable quantities of waste water that requires careful disposal. The use of peracetic acid as well in an aqueous medium produces large quantities of undiluted acetic acid, which cannot be concentrated and recycled economically. If, as is often necessary because of product stability, the peracetic acid is buffered during the process with an alkali carbonate solution and/or neutralized after the reaction with alkali hydroxide solution, strongly saline waste water is produced with considerable impact on the environment.

Use of organic percarboxylic acids in an organic solvent is therefore presumed to be advantageous. Thus, for example, the preparation of the previously described diepoxide by reaction of its parent diolefin with acetaldehyde monoperacetate or peracetic acid in ethyl acetate or acetone as solvent is old in the art (U.S. Pat. Nos. 2,716,123 and 2,804,473). At first glance, this type of operation seems very attractive. Nevertheless, it is not an optimal alternative due to the acetic acid which occurs as a coupled product. The acid must be separated from the reaction mixture and purified at considerable cost and its recovery is therefore not economically feasible.

The yields obtainable according to these known processes of 85.5% and a product purity of 86% are also very unsatisfactory (U.S. Pat. No. 2,716,123, Example IV). Moreover, the process of oxidizing acetaldehyde is not without risk, because explosive intermediates arise with this method.

It is recognized in the art that reaction mixtures obtained in this manner with per acids, because of their water and acid content, e.g., acetic acid, react very readily with the resulting epoxides to form by products such as glycols and glycol mono- and diesters (cf. German DE-AS No. 15 43 032). Therefore, epoxidation processes that employed performic or perpropionic acid, for example, appeared to be very difficult to carry out in an acid environment, because this resulted in cleavage of the oxirane ring (cf. German Patent DE-PS No. 29 16 834).

It is also noted in this regard that a percarboxylic acid solution with a mineral acid content less than 50 ppm is claimed in DE-OS No. 31 01 037 and in European Patent Application EP-OS No. 056 932, which describe the preparation of n-alkyloxiranes by means of perpropionic acid. According to the specification, the mineral acid content is preferably even less than 10 ppm. These processes relate to the preparation of monoepoxides.

However, according to the above teachings of prior art, it was to be expected that the preparation of diepoxides would be even more difficult with percarboxylic acid, because it was anticipated that acid would very likely undergo subsequent reactions due to the presence of the two partial epoxide structures.

Notwithstanding the negative expectations of the prior art, the invention has as its object the preparation of the abovementioned diepoxide utilizing perpropionic acid to obtain high yields and at the same time avoidance of interfering by product formation.

It has now been found that the object of the invention can be achieved by reacting the diolefin of the formula:

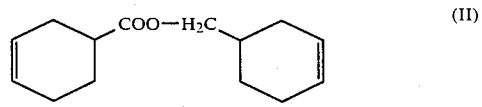 (II)

with a solution of perpropionic acid in benzene at a molar ratio of 1:2 to 1:3 (diolefin to perpropionic acid) at a temperature of 10° to 100° C.

Perpropionic acid can be prepared, for example, according to a process disclosed in West German Patent DE-PS No. 25 19 289 by reacting aqueous hydrogen peroxide with propionic acid in the presence of sulfuric acid, then extracting the resulting perpropionic acid with benzene from the reaction mixture The perpropionic acid in benzene solution obtained thereby can be purified still further to reduce the residual content of sulfuric acid, water, and hydrogen peroxide (cf. West German Patent DE-PS No. 25 19 290). However, a perpropionic solution is preferred that requires no further purification; in other words, the crude extract from the preparation of perpropionic acid can be used directly as such. This results in a considerably reduced technical expenditure.

Therefore, a perpropionic acid solution in benzene can be used that contains up to 1.5 weight percent of hydrogen peroxide, 1.5 weight percent of water, and up to 800 ppm of mineral acid.

According to the process of the invention, the diolefin is preferably used as such. However, it may be also diluted in a suitable solvent, e.g., benzene, whereby a wide range of concentrations can be freely selected.

The perpropionic acid solutions, which includes, inter alia, propionic acid, can contain from 10 to 30 weight percent of the per acid. Preferably, solutions with a per acid content of about 20 weight percent are employed.

A preferred molar ratio of diolefin to perpropionic acid is 1:2 to 1:2.4. An excess of per acid 3 to 15 mole percent is especially preferred.

Preferably, the reaction occurs at temperatures of 20° to 50° C. The novel process can be run at various pressures; in general, standard pressure is used, but the process can also be run at excess or subatmospheric pressure.

The reaction can be run both as a batch process or as a continuous process in reactors suitable for this type of reaction. Suitable reactors include agitated kettles, agitated kettle cascades, and tubular or loop-type reactors, whereby the heat of the reaction can be removed in any manner, e.g., by evaporative cooling or by internal or external cooling equipment.

Glass, special steel, or enameled material are suitable fabrication materials for the reactors for carrying out the process embodying the invention.

The perpropionic acid is combined with the diolefin or the solution thereof in a suitable solvent in any way desired. For example, both reactants can be introduced into the reactor together or in succession in any order of sequence. In a batch operating mode, the diolefin is preferably introduced first and the per acid is metered in while the reaction temperature is monitored. However, the reaction can also be performed in reverse order, i.e., the per acid is charged first and the olefin is metered in with temperature monitoring. If the reaction is run continuously, both reactants can be fed into the reactor separately or together If several series connected reactors are used, such as, for example, an agitated kettle cascade or a series of agitated kettles with a tubular reactor as the subsequent reactor, the addition of both the per acid and the diolefin can be distributed over several reactors. Although benzene is the preferred solvent, toluene, chlorobenzene, or halogenated aliphatics such as methylene chloride, chloroform and carbon tetrachloride can be used also to dissolve the diolefin.

No catalyst is required for the process of the present invention.

According to the process of the invention, a continuous mode of operation is very advantageous. According to this mode, the cycloaliphatic diolefin is charged with a solution of perpropionic acid in benzene at a molar ratio of 1:2 to 1:3 at the indicated temperature which is controlled within the range of 10° to 100° C. (preferably 20° to 50° C.) to a reactor system. This system consists of a series of 1 to 4 ideally mixed reactors and a subsequent reactor The residence time is controllably adjusted so that the conversion, based on the olefin double bonds used, is at least 80 mole percent downstream of the ideally mixed reactor(s) and at least 95, preferably over 98, mole percent downstream of the subsequent reactor. Then, the reaction mixture leaving the subsequent reactor is treated in a combination of distillation and desorption steps and is liberated from benzene, propionic acid, unreacted perpropionic acid, and other volatile components. This separation of the reaction mixture can be carried out according to one of the following variants, because the resulting diepoxide is the component with the highest boiling point in the mixture.

The invention is further illustrated by the drawings, wherein.

The following is a detailed description of the invention including various embodiments thereof with reference to the accompanying drawings.

EMBODIMENT 1

(Batch Process)

According to this embodiment, the individual components of the reaction mixture are removed in the order of their respective boiling points, individually or as a mixture by distillation or by distillation and desorption. In this process, the fractions of benzene, residues of perpropionic acid, propionic acid, and other readily volatile components are easily removed. The diepoxide remains as the bottoms. If desired, the separated benzene and the propionic acid can be returned to the per acid synthesis after additional purification steps.

EMBODIMENT 2

Figure 1:
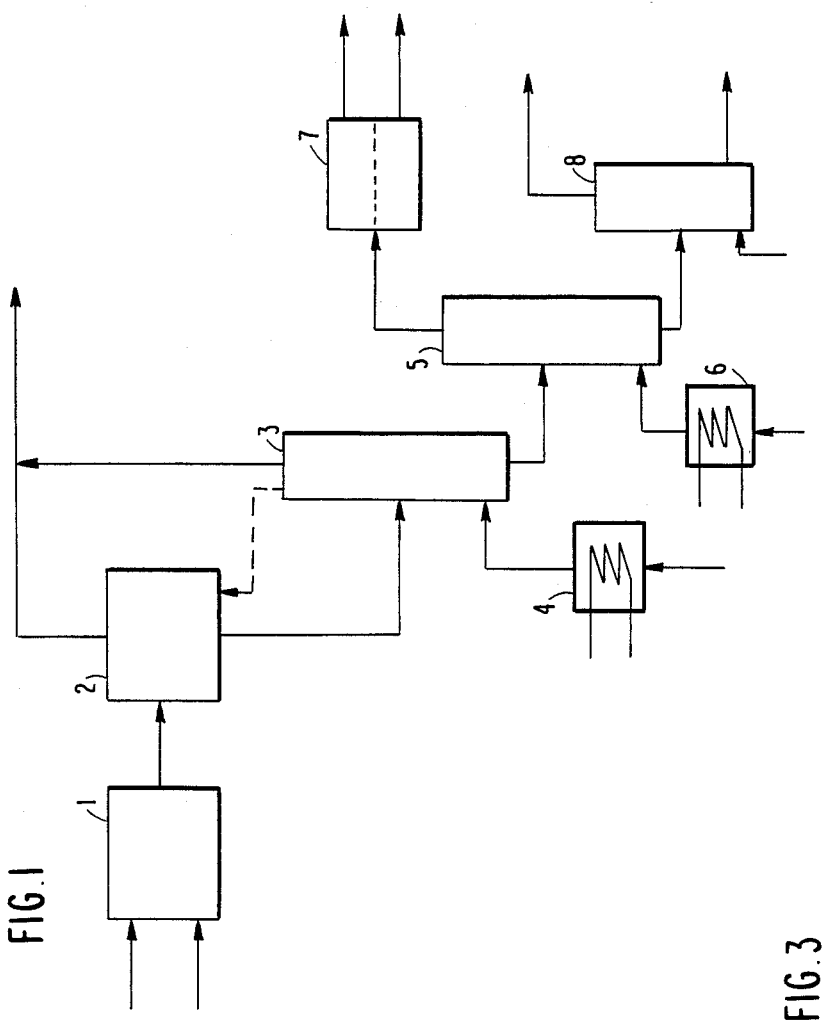
FIG. 1 is a flow diagram for a continuous process according to the invention.

(Continuous Process, FIG. 1)

According to this continuous variant of the process and as illustrated in FIG. 1, after the reaction mixture has left reaction unit 1, most of the benzene, propionic acid, and unreacted perpropionic acid are first removed in the one- or multistage distillation unit 2. Suitable for distillation devices are thin film, falling film, or circulation evaporators. Advantageously, distillation is effected at a reduced pressure of 0.5 to 600, preferably 10 to 300, mbar (temperature of the heating medium is 50° to 150° C.). Average residence times, based on the individual evaporation stages, are a maximum of 10 minutes, residence times of a maximum of 5 minutes being preferred.

According to the process of the invention, any amount of propionic acid remaining in the crude product is then removed by desorption in desorption unit 3 with benzene vapor that is generated in evaporator 4. The vapors from desorption unit 3 can either be conducted past distillation unit 2 or be passed therethrough. After this step, any remaining traces of benzene are desorbed from the diepoxide with steam from evaporator 6 in desorption unit 5 and/or with nitrogen or other inert gases in desorption unit 8. It is especially preferred to desorb first with steam, then with inert gases. The condensate from desorption unit 5 separates in phase separator 7 into an organic phase and water. The water is returned to evaporator 6, after enrichment, if necessary. The organic phase, which contains mostly benzene and propionic acid, is returned to perpropionic acid synthesis or to epoxidation after further processing, if necessary. Likewise, the streams of condensate consisting primarily of benzene and unreacted perpropionic and propionic acids and originating from distillation or desorption units 2 and 3, are returned, after further separation—cf. FIG. 3—which will be described below; to per acid synthesis or to epoxidation.

In all examples, devices such as, for example, the falling film evaporator, Sambay evaporator, columns with built in packing or fill packing material, or similar means that enable proper mass transfer between gaseous and liquid states and are known to those skilled in the art are suitable as the desorption unit.

EMBODIMENT 3

Figure 2:
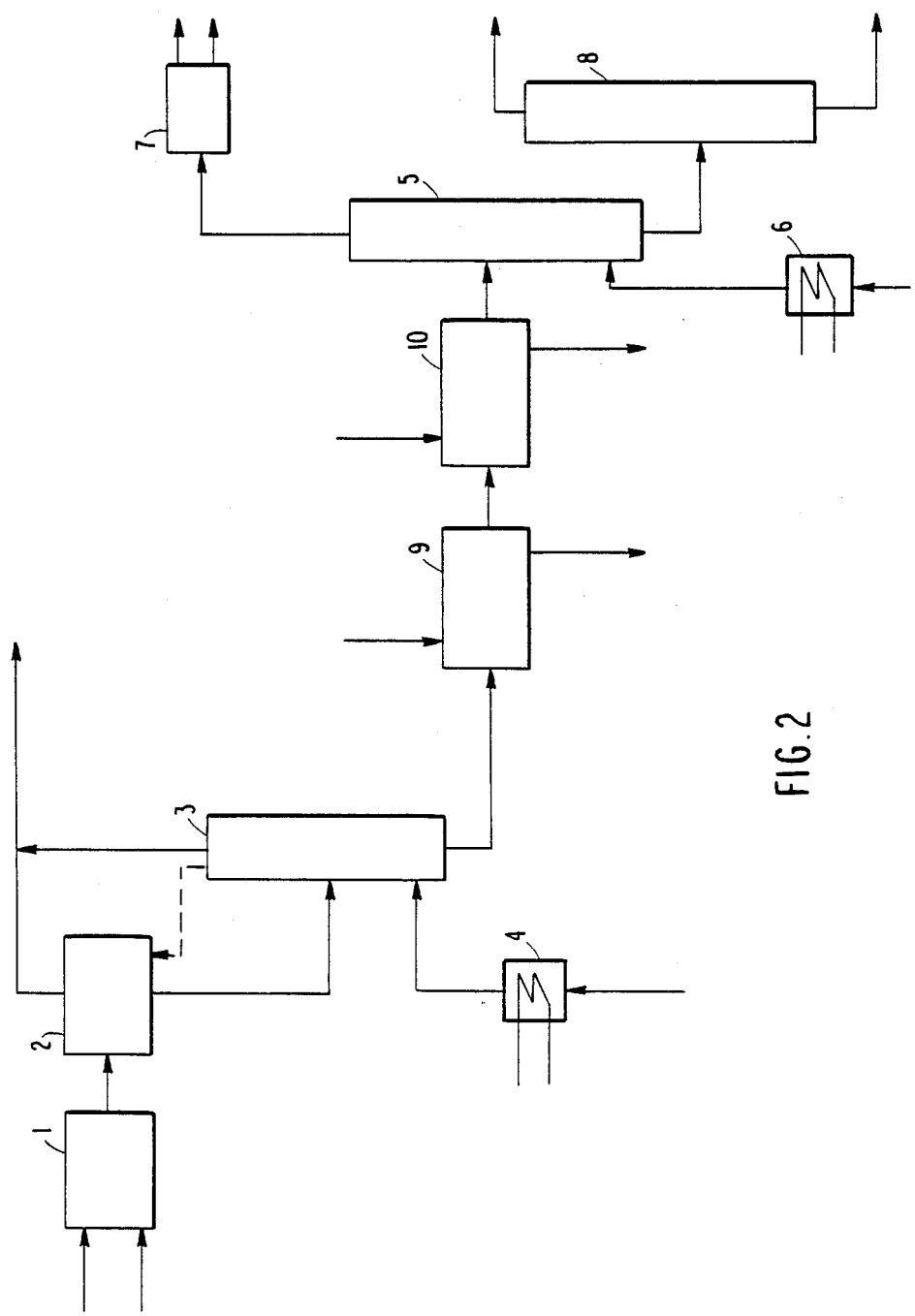
FIG. 2 is a flow diagram for a different continuous process according to the invention.

(Continuous Process, FIG. 2)

According to the third embodiment to be used in a continuous manner, benzene, unreacted perpropionic acid, and propionic acid, as in Embodiment 2, are removed in the one- or multistage distillation unit 2. Then, the remaining propionic acid is desorbed with benzene vapor in desorption unit 3. To remove the remaining traces of propionic acid, the crude epoxide is now washed with aqueous alkalies in the extraction 9, and then with water in the one- or multistage extraction unit 10. Suitable devices for these steps are various types of extraction columns or mixer settler units as well. The method of operation and design of such apparatus are well known to workers in the art. Solutions of, for example, NaOH, KOH, $Na_2CO_3$, $K_2CO_3$, $NaHCO_3$, $KHCO_3$, $NH_3$, etc., are suitable as aqueous alkali solutions, the concentrations of which can be freely selected over a wide range. An NaOH solution with a concentration of 0.2 to 15 weight percent, preferably 0.5 to 1.0 weight percent, is particularly preferred.

If mixer settler units are used for the water wash, the water can be supplied countercurrently, but each unit can also be operated with fresh water. Advantageously, a portion of the waste water from the mixer settler is used to prepare the alkali solution. The alkali and water washes can be carried out in a temperature range of 10° to 90° C.; temperatures between 30° to 70° C. are preferably. In the alkali wash, the weight ratio of the treated epoxide to alkali solution is 1:1 to 100:1 in the water wash, the ratio of epoxide flow rate to water flow rate is 1:1 to 100:1.

The water wash is followed by further progressing by desorption with steam and/or inert gas as described in Embodiment 2.

Figure 3:
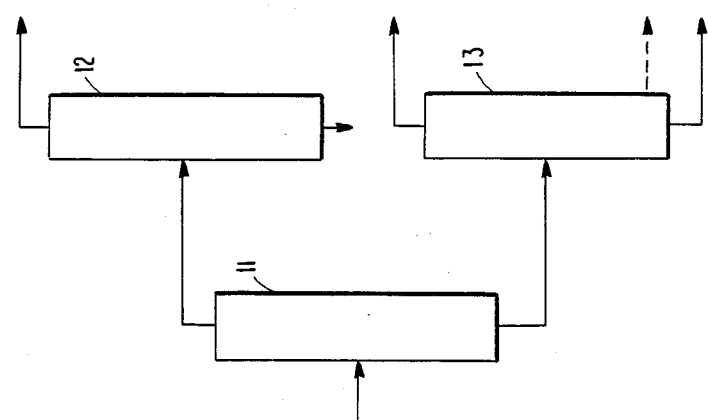
FIG. 3 is a flow diagram of a distillation system according to the invention.

In all embodiments of the invention resulting from a combination of distillation and desorption steps, condensates are obtained which are composed mainly of benzene, unreacted perpropionic acid, and other light boiling substances. According to the process of the invention, these materials are transferred to distillation unit 11 consisting of one or more columns (FIG. 3). This unit produces benzene as the overhead and in some cases other light boiling substances. In certain cases, the former is returned, after further distillation, to unit 12 for the preparation of perpropionic acid. A mixture of propionic acid, perpropionic acid, and benzene with a benzene proportions of 5 to 35 weight percent referred to the bottoms mixture, accumulates in the bottom of distillation unit 11. This mixture is fed to another distillation unit 13, in which the total amount of added benzene and perpropionic acid with portions of propionic acid is drawn off at the top. In so doing, a concentration of perpropionic acid in the distillate of 25 weight percent is not exceeded. This overhead is returned to the process of preparing perpropionic acid or to the reaction of the diolefin with perpropionic acid. Propionic acid is obtained as bottoms in column 13. After further processing such as by high purity distillation, the propionic acid is recycled to the preparation of perpropionic acid, after supplementing if necessary. It is of particular advantage to draw off the propionic acid obtained in unit 13 as a vapor above the bottoms and to condense it, thereby dispensing with one more purification step.

According to the invention, all distillation processing steps are preferably carried out at reduced pressure, e.g., 0.5 to 600 mbar. Columns in which benzene or propionic acid is obtained as overhead can likewise be run at standard pressure.

The novel process offers a series of surprising advantages. According to this process, it is possible via the so-called Prileschajew reaction to produce the abovementioned diepoxide on a commercial scale safely and with high yields. The product thus obtained is distinguished by its exceptional purity, high epoxide content, low viscosity, lack of odor, and light color.

The content of monoepoxide and ionic contaminants ($Na^+$, $Cl^-$, $Fe^{3+}$, etc.) is also very low, or not detectable. As a result, the product becomes available with clearly superior properties than diepoxide produced by other processes, with the abovementioned structure. Particularly for applications in the field of microelectronics, quality requirements are set forth the purity of the diepoxides to be employed there, which can readily be met by the process of the invention.

The process described herein is economical, since all auxiliary agents are recycled. The process is by no means harmful to the environment, because only water is the waste product from the oxidation agent. Moreover, only small amounts of other light boiling substances, and distillation residues are obtained, which can be disposed of safely and without serious problems.

According to the invention, only short reaction times are necessary, which makes the commercial operation highly cost effective.

It is surprising and unforeseeable that the reaction of the abovementioned diolefin with a crude perpropionic acid, which still contains mineral acid, water, and hydrogen peroxide in the concentrations mentioned above, can be carried out, and that side and secondary reactions are suppressed to the highest degree possible. Furthermore, it was unforeseeable that the reaction mixture thus obtained can be processed according to the invention by distillation or by distillation and desorption, without markedly reducing the epoxide content of the product.

The invention is further illustrated and described in the following examples.

EXAMPLE 1

(Batch)

A mixture of 270 g of propionic acid, 248 g of hydrogen peroxide (50%), and 155 g of concentrated sulfuric acid was stirred for 15 minutes at 35° C., then extracted with 500 g of benzene. The extract (748 g) had a perpropionic acid content of 20.7 weight percent. 170 g of tetrahydrobenzoic acid tetrahydrobenzyl ester was metered into this solution over a 15 minute period, with stirring and cooling to 40° C. This corresponds to a per acid-to-diolefin ratio of 2.23:1. The reaction was allowed to continue for 2 hours at 40° C. after the addition. The olefin conversion was greater than 99%, and the per acid conversion was 95.8%.

The clear solution (905 g) thus obtained was passed through a thin film evaporator over a 2 hour period at 95° C. and 120 mbar, during which benzene vapor was introduced countercurrently at the same time at the rate of 220 g per hour. 211 g of crude diepoxide accumulated at the bottom. This was again passed through a thin film evaporator at 95° C. and 65 mbar. Desorption with steam was carried out countercurrently at the same time.

194 g of almost colorless diepoxide with an epoxide content of 7.1 equivalents/kg and a viscosity of 330 mPa s (25° C.) was obtained as the bottoms.

EXAMPLE 2

(Continuous)

3.22 moles of perpropionic acid in benzene (about 22%, prepared according to West German Patent DE-PS No. 25 19 289, containing 0.57 weight percent of $H_2O_2$, 0.91 weight percent of $H_2O$, and 500 ppm of sulfuric acid, and used in Examples 2 to 5) and 1.43 moles of tetrahydrobenzoic acid tetrahydrobenzyl ester (which corresponds to a molar ratio of per acid to diolefin of 2.25:1) were charged hourly to the first agitated kettle of a reaction unit consisting of two agitated kettles with volumes of 300 ml and 600 ml, respectively, and a subsequent reactor designed as a tubular reactor with a volume of 790 ml. The reaction temperature in reactor 1 was 41° C., in reactor 2 it was 40° C., and in the subsequent reactor it was 46° C. Conversions of olefin were 91.1% downstream of the agitated kettle cascade, and 99.2% downstream of the tubular reactor. According to Process Embodiment 2, benzene, perpropionic acid, and propionic acid were separated first in a Sambay evaporator with a surface area of 0.065 $m^2$ at a temperature of 90° C. and a pressure of 100 mbar. The residual propionic acid was desorbed in a second evaporator of the same type and same surface area at 90° C. and 100 mbar at a flow rate of 315 g per hour of benzene vapor. All vapors in evaporator 2 were passed to evaporator 1 countercurrently to the product stream.

Subsequently, the epoxide was treated in two desorption units, each consisting of a Sambay evaporator (surface area of 0.065 $m^2$) with a packed column fitted to the bottom outlet (NW 25, 90 cm long, Raschig rings) at 100 mbar with 49 g per hour of steam and at 20 mbar with 36 g per hour of nitrogen at temperatures of 90° C.

331.4 g of diepoxide was obtained hourly as product with the following characteristics:

Viscosity (mPa·s, 25° C.): 270
Epoxide content (equivalents/kg): 7.57
Color number (Hazen): 40.

EXAMPLE 3

(Continuous)

3.13 moles of perpropionic acid in benzene (about 22%) and 1.40 moles of tetrahydrobenzoic acid tetrahydrobenzyl ester (which corresponds to a molar ratio of per acid to diolefin of 2.24:1) were charged hourly to the first agitated kettle of a reaction unit consisting of two agitated kettles with volumes of 200 ml and 400 ml, respectively, and a subsequent reactor designed as a tubular reactor with a volume of 1900 ml. The reaction temperature in reactor 1 was 41° C., in reactor 2 it was 37° C., and in the subsequent reactor it was 47° C. Conversions of olefin were 82.8% downstream to the agitated kettle cascade, and 99.2% downstream to the tubular reactor. According to Process Embodiment 2, benzene, perpropionic acid, and propionic acid were separated first in a Sambay evaporator with a surface area of 0.065 $m^2$ at a temperature of 90° C. and a pressure of 100 mbar. The residual propionic acid was desorbed in a second evaporator of the same type and same surface area at 90° C. and 100 mbar at a flow rate of 315 g per hour of benzene vapor. The vapors were treated as in Example 2.

Subsequently, the epoxide was treated in two desorption units, each consisting of a Sambay evaporator (surface area of 0.065 $m^2$) with a packed column fitted to the bottom outlet (NW 25, 90 cm long, Raschig rings) at 100 mbar with 49 g per hour of steam and at 20 mbar with 36 g per hour of nitrogen at temperature of 90° C.

349.9 g of diepoxide was obtained hourly as product with the following characteristics:

Viscosity (mPa·s, 25° C.) 295
Epoxide content (equivalents/kg): 7.59
Color number (Hazen): 25.

EXAMPLE 4

(Continuous)

3.04 moles of perpropionic acid in benzene (about 22%) and 1.40 moles of tetrahydrobenzoic acid tetrahydrobenzyl ester (which corresponds to a molar ratio of per acid to diolefin of 2.1:1) were charged hourly to the first agitated kettle of a reaction unit consisting of two agitated kettles with volumes of 300 ml and 600 ml, respectively, and a subsequent reactor designed as a tubular reactor with a volume of 1900 ml. The reaction temperature in reactor 1 was 40° C., in reactor 2 it was 40° C., and in the subsequent reactor it was 37° C. Conversions of olefin were 84.9% downstream of the agitated kettle cascade, and 97.8% downstream of the tubular reactor. According to Process Embodiment 3, benzene, perpropionic acid, and propionic acid were separated first in a Sambay evaporator with a surface area of 0.065 $m^2$ at a temperature of 90° C. and a pressure of 100 mbar. The residual propionic acid was desorbed in a second evaporator of the same type and same surface area at 90° C. and 100 mbar at a flow rate of 315 g per hour of benzene vapor. The vapors from evaporator 2 were not passed through evaporator 1. The crude epoxide thus obtained as bottoms was now washed in a mixer settler system with 1% sodium hydroxide solution (180 ml per hour), then washed with water in a series of three mixer settler units (180 ml per hour in each case). Subsequently, the epoxide was treated in two desorption units, each consisting of a Sambay evaporator (surface area of 0.065 m²) with a packed column fitted to the bottom outlet (NW 25, 90 cm long, Raschig rings) at 100 mbar with 49 g per hour of steam and at 20 mbar with 36 g hour of nitrogen at temperatures of 90° C.

337.4 g of diepoxide was obtained hourly as product with the following characteristics:
Viscosity (mPa·s, 25° C.): 288
Epoxide content (equivalents/kg): 7.32
Color number (Hazen): 30

EXAMPLE 5

(Continuous)

3.19 moles of perpropionic acid in benzene (about 22%) and 1.45 moles of tetrahydrobenzoic acid tetrahydrobenzyl ester (which corresponds to a molar ratio of per acid to diolefin of 2.20:1) were charged hourly to the first agitated kettle of a reaction unit consisting of two agitated kettles with volumes of 1500 ml and 700 ml, respectively, and a subsequent reactor designed as a tubular reactor with a volume of 1650 ml. The reaction temperature in reactor 1 was 39° C., in reactor 2 it was 34° C., and in the subsequent reactor it was 40° C. Conversions of olefin were 91.0% downstream to the agitated kettle cascade, and 99.6% downstream to the tubular reactor. According to Process Embodiment 3, benzene, perpropionic acid, and propionic acid were separated first in a Sambay evaporator with a surface area of 0.065 m² at a temperature of 90° C. and a pressure of 100 mbar. The residual propionic acid was desorbed in a second evaporator of the same type and same surface area at 90° C. and 100 mbar at a flow rate of 315 g per hour of benzene vapor. The vapors from evaporator 2 were not passed through evaporator 1. The crude epoxide thus obtained as bottoms was now washed in a mixer settler system with 1% sodium hydroxide solution (180 ml per hour), then washed with water in a series of three mixer settler units water (180 ml per hour in each case).

Subsequently, the epoxide was treated in two desorption units, each consisting of a Sambay evaporator (surface area of 0.065 m²) with a packed column fitted to the bottom outlet (NW 25, 90 cm long, Raschig rings) at 100 mbar with 49 g per hour of steam and at 20 mbar with 36 g per hour of nitrogen at temperatures of 90° C.

349.2 g of diepoxide was obtained hourly as product with the following characteristics:
Viscosity (mPa·s, 25° C.): 408
Epoxide content (equivalents/kg): 7.31
Color number (Hazen): 30

All percentages are weight percents even if not indicated in greater detail.

Variations and modifications of the foregoing will be apparent to those skilled in the art and are intended to be encompassed by the claims appended hereto.

We claim:

1. A process for the preparation of a cycloaliphatic diepoxide of the formula:

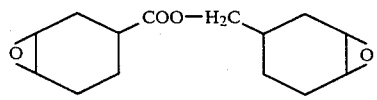 (I)

comprising reacting a diolefin of the formula:

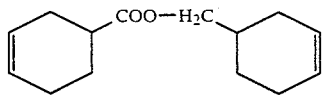 (II)

with a solution of perpropionic acid at a concentration of 10–30% by weight in benzene at a molar ratio of 1:2 to 1:3 (diolefin to perpropionic acid) comprising charging the cycloaliphatic diolefin together with the solution of perpropionic acid to a reactor system comprising a series of 1 to 4 ideally mixed reactors and a subsequent reactor, conducting the reaction at a temperature of 10° to 100° C., controlling the residence time so that the conversion, referred to the olefin double bonds used, is at least 80 mole percent downstream to the ideally mixed reactor(s) and at least over 98 mole percent downstream to the subsequent reactor, and separating the liberated propionic acid by a combination of distillation and desorption after the reaction to recover the desired product comprising removing benzene, propionic acid, small amounts of perpropionic acid, and other low-boiling substances from the mixture emerging from the subsequent reactor in a combination of distillation and desorption steps, wherein the distillation and desorption steps are carried out at reduced pressure of 10 to 300 mbar at temperatures of the heating medium of 50° to 150° C. and with residence time of a maximum of 5 minutes, in the separate steps, distilling off benzene and propionic acid, as well as small amounts of perpropionic acid, thereupon removing any amount of propionic acid remaining in the crude epoxide product by desorption with benzene vapor, thereafter driving off any remaining traces of the benzene and traces of propionic acid with steam and/or inert gas, and optionally initially washing the crude epoxide product with aqueous alkali, washing with water and thereafter carrying out desorption with steam and inert gases, wherein the perpropionic acid is prepared by reacting aqueous hydrogen peroxide with propionic acid in the presence of sulfuric acid, and then extracting the resulting perpropionic acid with benzene from the reaction mixture, wherein the perpropionic acid solution is the crude extract from the preparation of perpropionic acid which contains hydrogen peroxide, water and mineral acid and has a maximum content of 1.5 weight percent of hydrogen peroxide, 1.5 weight percent of water, and about 800 ppm of mineral acid.

2. The process according to claim 1, wherein the reaction is conducted at a temperature of 20° to 50° C.

3. The process according to claim 1, which is carried out continuously.

4. The process according to claim 1, further comprising obtaining a mixture by the combination of distillation and desorption, which mixture comprises benzene, propionic acid, small amounts of perpropionic acid, conducting said mixture to a distillation unit including at least two distillation columns, and in which there is a unit (12) for the process of preparing perpropionic acid, removing benzene, and any other low-boiling substances, from the top in a first distillation step, and returning the former to unit (12) for the process of preparing perpropionic acid after further distillation, and removing the total amount of perpropionic acid and propionic acid, as well as the portions of benzene at the bottom in amounts of 5 to 35 weight percent referred to the bottoms mixture, and passing the said bottoms mixture to a second distillation step in which the total amount of benzene and perpropionic acid contained therein with the portions of the propionic acid is removed at the top, while not exceeding a concentration of perpropionic acid in the overhead product of more than 25 weight percent, returning said overhead product to the reaction of perpropionic acid with olefin, and the propionic acid being drawn off as a vapor above the bottoms and condensed, is returned to unit (12) for the process of preparing perpropionic acid.

5. The process according to claim 1, further comprising obtaining a mixture by the combination of distillation and desorption, which mixture comprises benzene, propionic acid, small amounts of perpropionic acid, conducting said mixture to a distillation unit including at least two distillation columns, and in which there is a unit (12) for the process of preparing perpropionic acid, removing benzene and any other low boiling substances, from the top in a first distillation step, and returning the former to unit (12) for the process of preparing perpropionic acid after further distillation, and removing the total amount of perpropionic acid and propionic acid, as well as the portions of benzene at the bottom in amounts of 5 to 35 weight percent referred to the bottoms mixture, and passing the said bottoms mixture to a second distillation step in which the total amount of the benzene and perpropionic acid contained therein with the portions of propionic acid is removed at the top, while not exceeding a concentration of perpropionic acid in the overhead product of more than 25 percent, returning said overhead product to unit (12) for the process of preparing perpropionic acid, and the propionic acid being drawn off as a vapor above the bottoms and condensed, is returned to unit (12) for the process of prepared perpropionic acid.

6. The process as claimed in claim 1, wherein the molar ratio corresponds from about 1:2.20 to abut 1:2.25 and the perpropionic acid solution contains about 22 weight percent perpropionic acid, abut 0.57 weight percent hydrogen peroxide, about 0.91 weight percent water and about 500 ppm sulfuric acid as mineral acid.

* * * * *